United States Patent [19]
Sarantakis

[11] 3,941,763
[45] Mar. 2, 1976

[54] PGLU-D-MET-TRP-SER-TYR-D-ALA-LEU-ARG-PRO-GLY-NH$_2$ AND INTERMEDIATES

[75] Inventor: Dimitrios Sarantakis, West Chester, Pa.

[73] Assignee: American Home Products Corporation, New York, N.Y.

[22] Filed: Mar. 28, 1975

[21] Appl. No.: 563,258

[52] U.S. Cl. ............... 260/112.5 LH; 424/177
[51] Int. Cl.² ............... C07C 103/52; A61K 37/00
[58] Field of Search ............... 260/112.5 LH

[56] References Cited
UNITED STATES PATENTS

| | | | |
|---|---|---|---|
| 3,855,199 | 12/1974 | Foell et al. | 260/112.5 LH |
| 3,886,135 | 5/1975 | McKinley et al. | 260/112.5 LH |
| 3,886,137 | 5/1975 | Yardley | 260/112.5 LH |

*Primary Examiner*—Lewis Gotts
*Assistant Examiner*—Reginald J. Suyat
*Attorney, Agent, or Firm*—David E. Frankhouser

[57] ABSTRACT

The synthesis of the decapeptide pGlu-D-Met-Trp-Ser-Tyr-D-Ala-Leu-Arg-Pro-Gly-NH$_2$ by solid-phase techniques is described. The decapeptide inhibits LH release.

8 Claims, No Drawings

PGLU-D-MET-TRP-SER-TYR-D-ALA-LEU-ARG-PRO-GLY-NH₂ AND INTERMEDIATES

This invention relates to the novel decapeptide

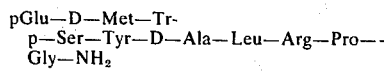

its process of synthesis, and to the novel intermediates formed in said synthesis.

The "luteinizing hormone releasing hormone" (hereinafter called "LRH") is the decapeptide L—p-Glu—His—Trp—Ser—Tyr—Gly—Leu—Arg—Pro—Gly—NH₂. This decapeptide is secreted by the hypothalamus and is carried to the pituitary where it stimulates the release of luteinizing hormone (LH) and follicle stimulating hormone (FSH) which control the ovulatory cycle. The present invention is concerned with a decapeptide which is a structural Modification of LRH and which inhibits release of LH from the pituitary.

In accordance with this invention, there is provided the decapeptide of the formula

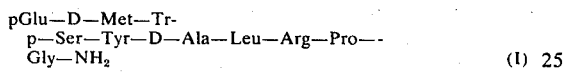

or a non-toxic salt thereof. Said decapeptide differs from LRH in that D-methionine is substituted for histidine in the two position, and D-alanine is substituted for glycine in the six position. In peptide shorthand, the decapeptide may be represented as D—Met-²—D—Ala⁶—LRH. All chiral amino acid residues identified in Formula (I) supra, and the other formulas set forth herein, are of the natural or L-configuration unless specified otherwise.

The decapeptide of Formula (I) inhibits the release of LH from the pituitary as demonstrated by standard in vitro and in vivo tests in laboratory animals. Thus, the decapeptide of the invention is useful for treating diseases or undesirable conditions characterized by excessive LH secretion, such as precocious puberty or the menopausal syndrome. Although certain other structural modifications of LRH, such as D—Phe²—D—Ala⁶—LRH, exhibit antiovulatory activity [See U.S. Pat. No. 3,855,199], the antiovulatory activity of the decapeptide of Formula (I) has not been demonstrated.

Also contemplated within the scope of the present invention are intermediates of the formula R⁴—p—Glu—D—Met—Trp—Ser(R³)—Tyr(R²)—D—Ala—Leu—Arg(Nᴳ—R¹)—Pro—Gly—R (II)

wherein:

R is selected from the class consisting of NH₂, OH, O-(lower)alkyl, in which (lower)alkyl is C₁ through C₆ (e.g. methyl, ethyl, pentyl, hexyl, etc.) and O-benzyl;

Nᴳ means the side chain nitrogen atoms of arginine; R¹ is a protecting group for the N^δ, N^ω and N^ω' nitrogen atoms of arginine selected from the class consisting of nitro, tosyl, benzyloxycarbonyl, adamantyloxycarbonyl and tert-butyloxycarbonyl; or R¹ is hydrogen which means there are no protecting groups on the side chain nitrogen atoms of arginine. Where the protecting group is nitro or tosyl, the protection is on either one of the N^ω, N^ω' nitrogens and in the case of benzyloxycarbonyl, or adamantyloxycarbonyl, the protection is on the N^δ nitrogen and either one of the N^ω, N^ω' nitrogen atoms. The preferred protecting group defined by R¹ is tosyl;

R² is a protecting group for the phenolic hydroxyl group of tyrosine selected from the class consisting of tetrahydropyranyl, tert-butyl, trityl, benzyl, 2,6-dichlorobenzyl, benzyloxycarbonyl and 4-bromobenzyloxycarbonyl. The preferred protecting group is benzyl; or R² is hydrogen which means there is no protecting group on the phenolic hydroxy function;

R³ is a protecting group for the alcoholic hydroxyl group of serine and is selected from the class consisting of acetyl, benzoyl, tetrahydropyranyl, tert-butyl, trityl, benzyl, 2,6-dichlorobenzyl, benzyloxycarbonyl or R³ is hydrogen which means there is no protecting group on the alcoholic oxygen atom. Preferably R³ is benzyl;

R⁴ is preferably hydrogen or an α-amino protecting group. The α-amino protecting groups contemplated by R⁴ are those known to be useful in the art in the step-wise synthesis of polypeptides. Among the classes of α-amino protecting groups covered by R⁴ are (1) acyl type protecting groups illustrated by the following: formyl, trifluoroacetyl, toluenesulfonyl (tosyl), benzensulfonyl, nitrophenylsulfenyl, tritylsulfenyl, o-nitro-phenoxyacetyl, chloroacetyl, acetyl, γ-chlorobutyryl, etc..; (2) aromatic urethan type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethan protecting groups illustrated by tert-butyloxycarbonyl, diisopropylmethoxycarbonyl, isopropyloxycarbonyl, ethoxycarbonyl, allyloxycarbonyl; (4) cycloalkyl urethan type protecting groups illustrated by cyclopentyloxycarbonyl, adamantyloxycarbonyl, cyclohexyloxycarbonyl; (5) thio urethan type protecting groups such as phenylthiocarbonyl; (6) alkyl type protecting groups as illustrated by triphenylmethyl (trityl), benzyl; (7) trialkylsilane groups such as trimethylsilane. The preferred α-amino protecting groups defined by R⁴ are selected from the class consisting of tert-butyloxycarbonyl, benzyloxycarbonyl and substituted benzyloxycarbonyl.

In Formula (II) at least one of R¹, R², or R³ is a protecting group.

A further aspect of the present invention relates to intermediates linked to a solid resin support. These intermediates are represented by the formula:

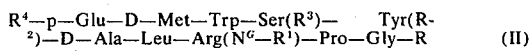

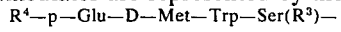

wherein:

R¹, R², R³, and R⁴ have the same meaning as in Formula II;

A is an anchoring bond used in solid phase synthesis linked to a solid resin support. A is selected from the class consisting of:

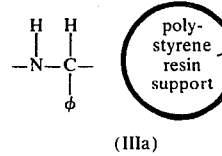 and 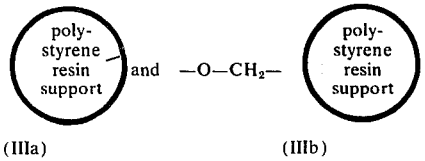

(IIIa)         (IIIb)

The symbol φ means "phenyl." The polystyrene resin support is preferably a copolymer of styrene with about 1 to 2% divinyl benzene as a cross linking agent which causes the polystyrene polymer to be completely insoluble in most organic solvents. The polystyrene polymer is composed of long alkyl chains bearing a phenyl ring on every second carbon and the terminal amino acid residue (Gly) is joined through a covalent carbon to nitrogen or oxygen bond to these phenyl rings. The alkyl chains are cross linked at approximately every fiftieth carbon by p-substituted phenyl residues derived from divinyl benzene.

In selecting a particular side chain protecting group to be used in the synthesis of the peptides of Formula (I), the following rules should be followed: (a) the protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

Illustrative of pharmaceutically acceptable non-toxic salts of Formula I are hydrochloride, hydrobromide, sulfate, phosphate, maleate, acetate, citrate, benzoate, succinate, malate, ascorbate, and the like.

The peptides of Formula (I) through (III) are prepared using solid phase synthesis. The synthesis is commenced from the C-terminal end of the peptide using an α-amino protected resin. Such a starting material can be prepared by attaching an α-amino protecting glycine to a benzhydrylamine resin, a chloromethylated resin or a hydroxymethyl resin, the former being preferred. The preparation of a benzhydrylamine resin is described by P. Rivaille et al., Helv. 54, 2772 (1971) and the preparation of the hydroxymethyl resin is described by Bodanszky et al., Chem. Ind. (London) 38, 1597-98 (1966). A chloromethylated resin is commercially available from Bio Rad Laboratories Richmond, California and the preparation of such a resin is described by Stewart et al., "Solid Phase Peptide Synthesis" (Freeman & Co. San Francisco 1969), Chapter 1, pp. 1–6. In using the benzhydrylamine resin an amide anchoring bond is formed with the α-amino protected glycine as follows:

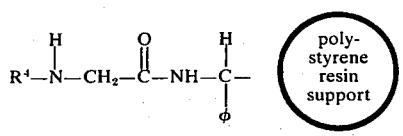

This permits the C-terminal amide function to be obtained directly after the amino acid sequence in the synthesis is complete by cleaving off the resin support to form the glycine amide at the C-terminal portion of the desired peptide of Formula (I). When the other resins are used, the anchoring bond is the benzylester group as defined supra in Formula (IIIb), which after cleavage of the peptide from the resin support must be converted to the C-terminal amide. The preferred procedure is to ammonolyse the protected peptide off the resin and then remove the protecting group by hydrogenolysis or by hydrogen fluoride cleavage. An alternate procedure would be to cleave by transesterification with methanol/Et)$_3$N and then convert the resulting ester into an amide and subsequently deprotect as described above. See J. M. Stewart "Solid Phase Peptide Synthesis", pp. 42–46 (W. H. Freeman & Co. 1968).

The α-amino protected glycine is coupled to the benzhydrylamine resin with the aid of a carboxyl group activating compound such as dicyclohexylcarbodiimide. Following the coupling of the α-amino protected glycine to the resin support, the α-amino protecting group is removed such as by using trifluoroacetic acid in methylene chloride, trifluoroacetic acid alone or HCl in dioxane. The deprotection is carried out at temperature between about 0°C and room temperature. Other standard cleaving reagents and conditions for removal of specific α-amino protecting groups may be used as described in Schroder & Lubke, "The Peptides," 1, 72–75 (Academic Press 1965). After removal of the α-amino protecting group the remaining α-amino protected amino acids are coupled step-wise in the desired order to obtain a compound of Formula (I). However, as an alternate to adding each amino acid separately to the reaction, some of them may be coupled prior to addition to the solid phase reactor. If the C-terminal end of the peptide unit is represented by glycine or proline and the coupling is carried out with DCC, a mininum of racemization is encountered with proline and no problems are encountered with glycine which has no asymmetric centre. Each protected amino acid or amino acid sequence, is introduced into the solid phase reactor in about a four-fold excess and the coupling is carried out in a medium of dimethylformamide: methylene chloride (1:1) or in dimethylformamide or methylene chloride alone. In cases where incomplete coupling occurred the coupling procedure is repeated before removal of the α-amino protecting group, prior to the coupling of the next amino acid to the solid phase reactor. The success of the coupling reaction at each stage of the synthesis is monitored by the ninhydrin reaction as described by E. Kaiser et al., Analyt. Biochem, 34, 595 (1970)

After the desired amino acid sequence has been synthesized, the peptide is removed from the resin support by only with a reagent such as hydrogen fluoride which not onnly cleaves the peptide from the resin but also cleaves all remaining side chain protecting groups and the α-amino protecting group (if present) on pyroglutamic acid to obtain directly a compound of Formula I in the case where the benzhydrylamine resin was used. Where a chloromethylated resin is used the peptide may be separated from the resin by methanolysis after which the recovered product is chromatographed on silica gel and the collected fraction subject to ammonolysis to convert the methyl ester to the C-terminal amide. Any side chain protecting group may then be cleaved as previously described or by other procedures such as catalytic reduction (e.g. Pd on C) using conditions which will keep the Trp moiety intact. When using hydrogen fluoride for cleaving, anisole is included in the reaction vessel to prevent the oxidation of labile amino acid (e.g. tryptophan).

The solid phase synthesis procedure discussed supra is well known in the art and has been essentially described by M. Monahan et al., C. R. Acad. Sci. Paris, 273, 508 (1971).

The nomenclature used for peptide is described by Schroder & Lubke, supra, pp viii–xxix and in Biochemistry, 11, 1726–1732 (1972).

The following examples are illustrative of the preparation of the compounds of Formulas I through III.

Example I

N-Benzyloxycarbonyl-L-pyroglutamyl-p-methionyl-L-tryptophyl-O-benzyl-L-seryl-O-2,6-dichlorobenzyl-L-tyrosyl-D-alanyl-L-leucyl-$N^a$-tosyl-L-arginyl-L-prolyl-glycyl resin Benzhydrylamine hydrochloride resin (20 g.; theor. available amine 0.4 mmoles per gram) is placed in a Merrifield solid phase flask and is treated with the following wash cycle.

a. trifluoroacetic acid-methylene chloride (1:1) containing 5% 1,2-ethane dithiol (30 minutes)
b. methylene chloride (3 times)
c. dimethylformamide
d. 10% triethylamine in dimethylformamide (v/v) (twice for 5 minutes each time)
e. dimethylformamide
f. methylenechloride (3 times)

Unless indicated otherwise, each wash is allowed a contact time of at least one and one-half minutes. After the wash cycle is completed, the resin is tested for reactive amino groups by the ninhydrin test according to the procedure of Kaiser, supra, and is shown to give a positive reaction.

In order to attach the first amino acid residue, the resin so prepared is treated with tert-butyloxycarbonyl glycine (25 mmoles) in methylene chloride and then, in two portions, with N,N-di-isopropylcarbodiimide (30 mmoles) in methylene chloride over a period of 30 minutes. The mixture is shaken for at least 4 hours and finally filtered. The peptide-resin is then washed successively with methylene chloride (three times), dimethylformamide, and methylene chloride (three times). To test for completion of reaction, the peptide resin is subjected to a ninhydrin test and is shown to give a negative reaction.

The deprotection of the attached amino acid is carried out by treating the peptide-resin with trifluoroacetic acid - methylene chloride (1:1) containing 5% 1,2-ethane dithiol (first for 10 minutes then for 20 minutes) and then performing the wash cycle as described above [steps (b) through (f)]. Again, a sample of the peptide-resin is subjected to the ninhydrin test and is shown to be strongly positive, indicating deprotection of the glycine molecule attached to the resin.

The following amino acid residues are then introduced consecutively: BOC-L-proline, BOC-$N^a$-tosyl-L-arginine, and BOC-L-leucine. Each coupling step and deprotection step is performed as described above for the preparation of the glycine-resin. Part of the tetrapeptide so produced (3 g.) is treated consecutively as described above with 6 m moles of the following amino acids: BOC-D-alanine, BOC-O-2,6-dichlorobenzyl-L-tyrosine, BOC-O-benzyl-L-serine, BOC-L-tryptophan, BOC-D-methionine, and finally $N^\alpha$-benzyloxycarbonyl-L-pyroglutamic acid. Yield of title product: 3.7 g. The abbreviation BOC means the tertbutyloxycarbonyl group.

Example II

L-Pyroglutamyl-D-methionyl-L-tryptophyl-L-seryl-L-tyrosyl-D-alanyl-L-leucyl-L-arginyl-L-prolyl-glycine The peptide-resin prepared according to Example I (3.5 g) is mixed with 5 ml anisole and treated under vacuo and at 20°C with 100 ml liquid hydrofluoric acid for 45 minutes. The excess hydrofluoric acid is removed under vacuo as fast as pssible (45–60 minutes) and the residue is treated with 10% aq.-acetic acid (ca. 150 ml) then filtered and the filtrate extracted with ether. The aqueous phase is separated and lyophilized to afford 900 mg of crude product.

The above crude product is taken in a small volume of the upper phase of a biphasic mixture of n-butanol — 0.1 M ammonium acetate (1:1, v/v) and applied onto a column (2.5 × 90 cm) of Sephadex G-25 which is equilibrated first with the lower phase then with the upper phase of the above mixture. The column is eluted with the upper phase and fractions of 4.8 ml each are collected with the help of an automatic fraction collector. The emergence of the product is followed by the Folin-Lowry method and the fraction tubes 25–41 are pooled and lyophilized to give 386 mg of the title decapaptide as the acetate. Rf (n-butanol-water-gl. acetic acid, 4:5:1, v/v/v) 0.70 and Rf (iso-amyl alcohol-water-pyridine, 7:6:7, v/v/v) 0.79. Ser 0.91, Glu 1.01, Pro 1, Gly 1, Ala 0.97, Met 0.96, Leu 1.03, Tyr 0.84, $NH_3$ 1.28, Arg 1.01, Trp. N.D.

Example III

A. The inhibition of LRH-induced release of LH from the pituitary is demonstrated in vitro in rat pituitary tissue cultures by the method of Vale et al., Endrocinology, 91, 562 (1972) as modified by Grant et al., B. B. R. C., 51, 100 (1973). LH concentration is determined by double-antibody radioimmunoassay. The results of the in vitro testing are set forth below:

| LRH | Concentration, ng/ml D—$Met^2$—D—$Ala^6$—LRH | LH |
|---|---|---|
| — | — | 92±8 |
| 5 | — | 282±11 |
| 5 | 1000 | 92±2 |
| 5 | 100 | 143±2 |
| 5 | 10 | 308±2 |

B. The inhibition of LRH-induced release of LH is demonstrated in vivo in rats as follows:

Male Sprague-Dawley rats are divided into two groups of at least 5 animals in each group. One group receives the test compound. The other is the control group (no test compound). At zero time, the test group receives a 100-ng dose (subcutaneous) of D—$Met^2$—D—$Ala^6$—LRH in 0.2 ml. of physiological saline, while the control group receives a 0.2 ml. dose of physiological saline alone. At 20 minutes, blood samples are removed by cardiac puncture, and LH concentration is determined by double-antibody radioimmunoassay. At 45 minutes, the zero-time dose is repeated for each group of animals. At 50 minutes, the animals in each group are given a 200-ng dose (subcutaneous) of LRH in 0.2 ml. of physiological saline. A second blood sample is removed by cardiac puncture at 70 minutes and LH concentration is determined. The results of the assays for LH plasma concentration are given below:

| Time | LH Plasma Conc. (ng/ml) | |
| --- | --- | --- |
| | Control | D—Met²—D—Ala⁶—LRH |
| 20* | 5±07 | 10±4 |
| 70** | 129±20 | 25±5 |

*before LRH administration
**after LRH administration

What is claimed is:
1. A compound selected from the group consisting of
L—P—Glu—D—Met—L—Trp—L—Ser—L—Tyr—D—Ala—L—Leu—L—Arg—L—Pro—Gly—NH₂ and

R⁴—L—p—Glu—D—Met—L—Trp—L—Ser(R³)—L—Tyr—(R²)—D—Ala—L—Leu—L—Arg(-Nᴳ—R¹)—L—Pro—Gly—R or a non-toxic salt thereof; wherein
R is selected from the class consisting of NH₂, OH, O-(lower)alkyl and O-benzyl; $R^1$ is selected from the class consisting of hydrogen and a protecting group for the $N^\delta$, $N^\omega$, and $N^{\omega'}$ nitrogen atoms of arginine selected from nitro, tosyl, benzyloxycarbonyl and adamantyloxycarbonyl;
$R^2$ is selected from the class consisting of hydrogen and a protecting group for the phenolic hydroxyl group of tyrosine selected from tert-butyl, tetrahydropyranyl, trityl, benzyl, 2,6-dichlorobenzyl, benzyloxycarbonyl and 4-bromobenzyloxycarbonyl;
$R^3$ is selected from the class consisting of hydrogen and a protecting group for the alcoholic hydroxyl group of serine and is selected from acetyl, benzoyl, tetrahydropyranyl, tertbutyl, trityl, 2,6-dichlorobenzyl, benzyl and benzyloxycarbonyl;
$R^4$ is selected from the class consisting of hydrogen and an α-amino protecting group; with the proviso that at least one of $R^1$, $R^2$, and $R^3$ is a protecting group.

2. A compound according to claim 1 wherein R is NH₂.

3. A compound according to claim 1 wherein R is NH₂, $R^1$ is tosyl, $R^2$ is 2,6-dichlorobenzyl, $R^3$ is benzyl and $R^4$ is benzyloxycarbonyl.

4. A compound according to claim 1 which is selected from L-pGlu-D-Met-L-Trp-L-Ser-L-Tyr-D-Ala-L-Leu-L-Arg-L-Pro-Gly-NH₂ and a non-toxic acid addition salt thereof.

5. A compound of the formula:
R⁴—L—p—Glu—D—Met—L—Trp—L—Ser(R³)—L—Tyr(R²)—D—Ala—L—Leu—L—Arg—(Nᴳ—R¹)—L—Pro—Gly—A wherein:
$R^1$ is selected from the class consisting of hydrogen and a protecting group for the $N^\delta$, $N^\omega$ and $N^{\omega'}$ nitrogen atoms of arginine selected from nitro, tosyl, benzyloxycarbonyl and adamantyloxycarbonyl;
$R^2$ is selected from the class consisting of hydrogen and a protecting group for the phenolic hydroxyl group of tyrosine selected from tert-butyl, tetrahydropyranyl, trityl, benzyl, 2,6-dichlorobenzyl, benzyloxycarbonyl and 4-bromobenzyloxycarbonyl;
$R^3$ is selected from the class consisting of hydrogen and a protecting group for the alcoholic hydroxyl group of serine and is selected from acetyl, benzoyl, tetrahydropyranyl, tert-butyl, trityl, 2,6-dichlorobenzyl, benzyl and benzyloxycarbonyl;
$R^4$ is slected from the class consisting of hydrogen and an α-amino protecting group; and A is selected from the class consisting of

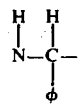 and 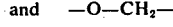

wherein said polystyrene resin is cross linked through the phenyl group on each second carbon atom of the alkyl chain of said polystyrene.

6. A compound according to claim 5 wherein $R^4$ is an α-amino protecting group which is selected from the class consisting of benzyloxycarbonyl, tert-butyloxycarbonyl, cyclopentyloxycarbonyl, tert-amyloxycarbonyl and isobornyloxycarbonyl.

7. A compound according to claim 5 wherein A is a benzhydrylamine resin and $R^4$ is benzyloxycarbonyl.

8. A compound according to claim 7 wherein $R^1$ is tosyl, $R^2$ is 2,6-dichlorobenzyl and $R^3$ is benzyl.

* * * * *